United States Patent [19]

Sommer

[11] Patent Number: 5,061,065
[45] Date of Patent: Oct. 29, 1991

[54] PARTICLE CONTAMINATION DETECTION IN FLUIDS THROUGH THE EXTERNAL SECTION OF A LASER

[75] Inventor: Holger T. Sommer, Greenbelt, Md.

[73] Assignee: Pacific Scientific Company, Silver Spring, Md.

[21] Appl. No.: 424,711

[22] Filed: Oct. 20, 1989

[51] Int. Cl.⁵ ............................................. G01N 21/05
[52] U.S. Cl. .................................... 356/246; 356/338; 372/98
[58] Field of Search ............... 356/336, 338, 339, 246, 356/440; 372/92, 98

[56] References Cited

U.S. PATENT DOCUMENTS

| | | | |
|---|---|---|---|
| 4,019,056 | 4/1977 | Block et al. | 250/344 |
| 4,253,770 | 3/1981 | Horiba | 356/433 |
| 4,544,274 | 10/1985 | Cremers et al. | 356/436 |
| 4,547,075 | 10/1985 | Fei | 356/246 |
| 4,565,448 | 1/1986 | Abbott et al. | 356/246 |
| 4,792,233 | 12/1988 | Irvine | 356/246 |
| 4,798,465 | 1/1989 | Knollenberg | 356/336 |
| 4,842,406 | 6/1989 | VonBargen | 356/336 |

Primary Examiner—Richard A. Rosenberger
Attorney, Agent, or Firm—Lane, Aitken & McCann

[57] ABSTRACT

In a particle detecting instrument, a particle detecting cell comprises a laser plasma tube in combination with a glass prism through which a fluid channel is defined. The glass prism abuts the transmitting end of the laser plasma tube and the end wall of the prism is arranged at the brewster angle with respect to the plasma tube axis. The fluid channel defined in the prism is also arranged at the brewster angle with respect to the laser beam passing through the prism. A mirror is provided on the prism to reflect the light back through the prism into the plasma tube. The mirror is positioned so that the light reflected back into the plasma tube is in phase with the light amplified within the plasma tube. A mount is provided for the mirror to adjust its lateral and angular position. In an alternative embodiment, the plasma tube abuts a glass window pane defining one side wall of a fluid channel to receive a gas entraining particles to be measured.

12 Claims, 3 Drawing Sheets

PARTICLE CONTAMINATION DETECTION IN FLUIDS THROUGH THE EXTERNAL SECTION OF A LASER

BACKGROUND OF THE INVENTION

This invention relates to particle size measuring instruments and more particularly to instruments which measure the particle size entrained in a fluid stream by means of the light scattered from the particles as they pass through a laser beam.

In U.S. Pat. No. 4,842,486, issued June 27, 1989, invented by Kenneth P. VonBargen, and assigned to the assignee of this application, there is disclosed a particle size measuring instrument of the type to which the present invention pertains. As disclosed in the above-identified application, the particles entrained in a fluid stream are caused to flow through a laser beam in an enclosed channel and light scattered from the particles as they pass through the beam are detected by photodetectors. The height and length of the pulses generated by the photodetectors in response to the particles provide an indication of the size of the particles.

In the above described system, the ability of the instrument to distinguish the pulses caused by particles from noise depends upon the amplitude of the pulses generated. By increasing the intensity of the laser beam, the amount of light scattered from the particles and, thus, the amplitude of the pulses generated by a given particle size can be increased. Accordingly, smaller particles can be detected.

SUMMARY OF THE INVENTION

In accordance with the present invention, the intensity of the laser being encountered by the particles is increased by forming the fluid cell in a section of the laser between the section in which light amplification takes place and an external mirror which reflects light back into the light amplifying section in phase with the laser beam being amplified in the light amplifying section. This section of the laser between the external mirror and the light amplifying section is referred to as the external laser section and is similar to the external cavity of an external cavity laser, except that in the applicant's invention, the external laser section is not a cavity. In order for the laser to generate a laser beam with the fluid cell in the external laser section, the losses at interfaces between media of different optical properties in the laser must be minimized. This is achieved in accordance with the present invention by employing a prism to define the channel through which the fluid passes. One wall of the prism is positioned at and defines the end wall of the plasma tube of the laser and is arranged at the brewster angle with respect to the axis of the plasma tube and, therefore, at the brewster angle with respect to the laser beam within the plasma tube so that losses at this interface are minimized. The laser beam will be refracted at this interface and be transmitted linearly through the prism, passing through the channel defined in the prism for the fluid stream. The walls of the channel through which the laser beam passes are also arranged at the brewster angle relative to the laser beam in the prism. In the preferred embodiment, the fluid flowing through the channel is considered to be water and the brewster angles at the interfaces of the channel are based on this consideration. The external mirror defining one side of the external laser section is mounted directly on the prism on the opposite side of the channel from the end wall of the plasma tube. By employing brewster angles at the interface with the plasma tube and the prism and between the prism and the fluid channel defined in the channel, the losses at these interfaces are minimized and, the laser will operate and generate a high intensity beam passing through the fluid stream in the channel.

DESCRIPTION OF SPECIFIC EMBODIMENTS

Figure 1:
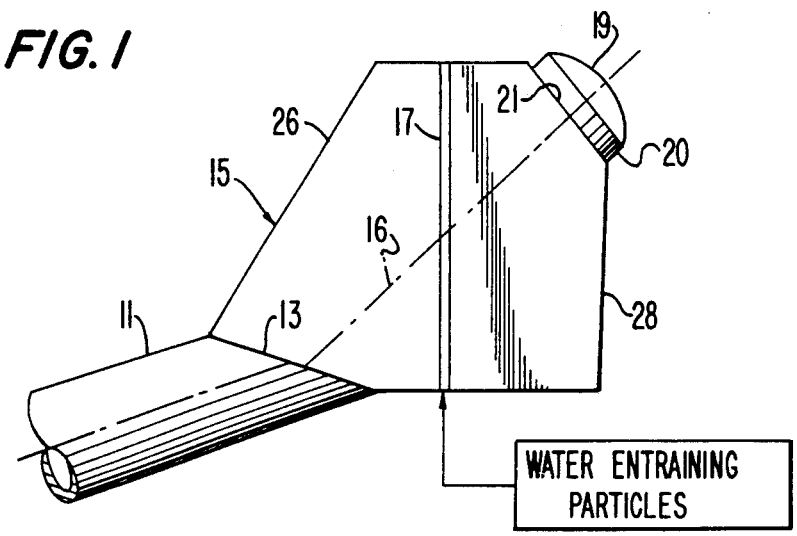
FIG. 1 is a side view in elevation of the particle detecting cell of the invention.
Figure 2:
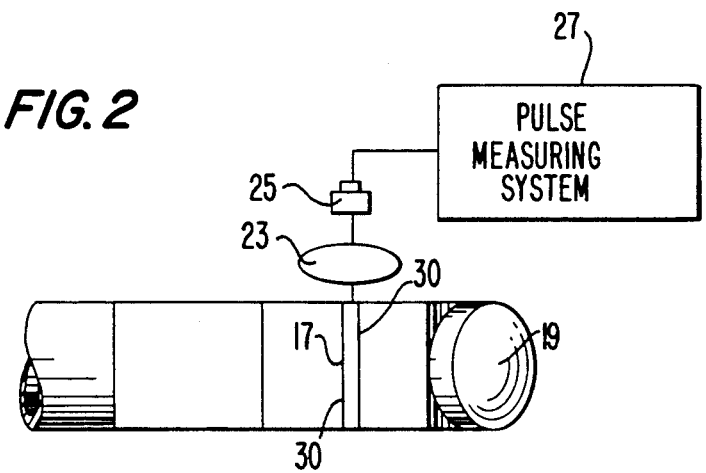
FIG. 2 schematically illustrates the particle measuring instrument of the invention showing a top plan view of the particle cell of FIG. 1.

The embodiment illustrated in FIG. 1 is designed for a particle detection system in which the particles are entrained in water or any other liquid which has the same coefficient of refraction as water. As shown in FIG. 1, the system of the invention comprises a gas laser plasma tube 11, the beam transmitting end of which abuts against the outside wall 13 of a prism 15. The wall 13 is oriented at the brewster angle with respect to the axis of the plasma tube 11 and the laser beam amplified within the plasma tube 11. For convenience of manufacture, the plasma tube may be provided with its own window of the same material as the prism 13, which abuts against the wall 13 of the prism. Alternatively, the wall 13 may interface directly with the gas of the plasma tube. In the preferred embodiment, the prism 15 is made of BK7 glass having an index of refraction of 1.5147 at a wavelength of 694 nanometers. With this glass, the brewster angle, which is the angle between the perpendicular to the end wall surface and the axis of the plasma tube 11 is 56.56 degrees. The laser beam is refracted at the interface defined by the wall 13 and travels through the prism 15 along a different axis 16 than the axis of the plasma tube 11. Extending through the prism 15 is a narrow water channel 17 which is rectangular in cross section having a long dimension of 2.00 millimeters and a short dimension of 1.00 millimeter. The channel 17 passes vertically through the middle of the prism and is arranged so that the laser beam passes through the channel 17 across the short dimension of the cross section through the channel. The side walls of the channel 17 through which the laser beam passes are both arranged at the brewster angle with respect to the laser beam. This brewster angle for the beam passing from BK7 glass into water is 53.06 degrees. A spherical mirror 19 is formed on a spherically curved wall of a block 20 of the BK7 glass. The block 20 has a flat bottom surface supporting on a flat surface 21 of the prism centered on and perpendicular to the laser beam axis in the prism. A thin film of index matching liquid separates the block 20 from the prism 15. The mirror 19 acts as an external mirror for the laser in that it and a mirror (not shown) on the back end of the plasma tube 11 repeatedly reflect light back and forth between them in phase, with amplification of the light wave being effected in the plasma tube 11. With this arrangement, the laser will generate an intense laser beam in the external laser section defined between the end wall 13 and mirror 19. Particles in the liquid passing through the laser beam will scatter light from the laser beam sideways. This sideways scattered light is collected by a lens 23 positioned at the side of the prism 15 as shown in FIG. 2 and the lens 23 focuses the light onto a photodetector 25. In this manner, each particle entrained in the liquid stream passing through the laser beam in the channel 17 will cause the photodetector 25 to generate a pulse, the amplitude of which will be an indication of the size of the particle. The output pulses from the photodetector 25 are applied to a pulse amplitude measuring system 27 which operates to measure the amplitude of each pulse produced by the photodetector and thus provide a measurement of each particle in the liquid stream passing through the channel 17. The pulse amplitude measurement system may be like that disclosed in the above-mentioned U.S. Pat. No. 4,842,406.

The prism 15 comprises a one-piece glass block section 26, a one-piece glass block section 28, and glass spacers 30 all made of the same glass and having the same index of refraction. The spacers 30 are sandwiched between the glass block sections 26 and 28 and are spaced from each other to define the fluid channel 17 through the prism. The spacers 30 are cemented to the glass block sections 26 and 28 with transparent cement having the same index of refraction as the spacers and the glass block sections.

Figure 3:
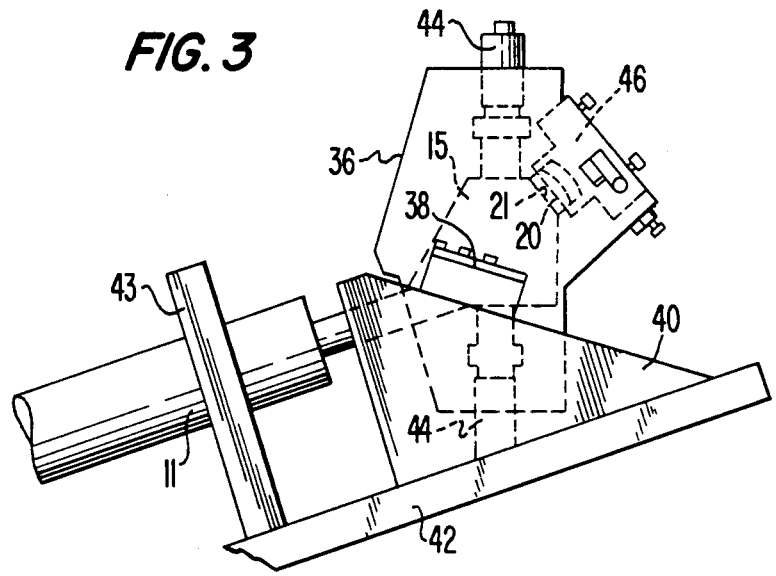
FIG. 3 shows the particle detecting cell of FIG. 1 in combination with mounting structure for supporting the particle detecting cell.
Figure 6:
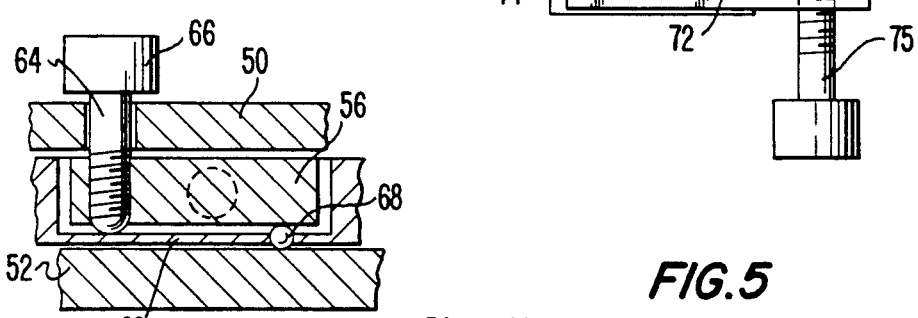
FIG. 6 is a sectional view taken along line 6—6 of FIG. 4 showing a lever mechanism used in the fixture of FIG. 4.

As shown in FIG. 3, the prism 15 is mounted within a hollow frame 36, which in turn is mounted by brackets 38 on a pair of rails 40. The frame 36 extends down between the rails 40 which are mounted on a base 42. The laser plasma tube 11 is also mounted on the base 42 by means of brackets 43. The frame 36 supports connecting hardware 44, which in turn provides connections for tubing, which provide the water flow passing through the passageway 17 in the prism 15 as shown in FIG. 1. The frame 36 also supports a fixture 46 for adjusting the position of the mirror block 20 on the prism 15. This fixture is more clearly shown in the drawings of FIGS. 4-6.

Figure 4:
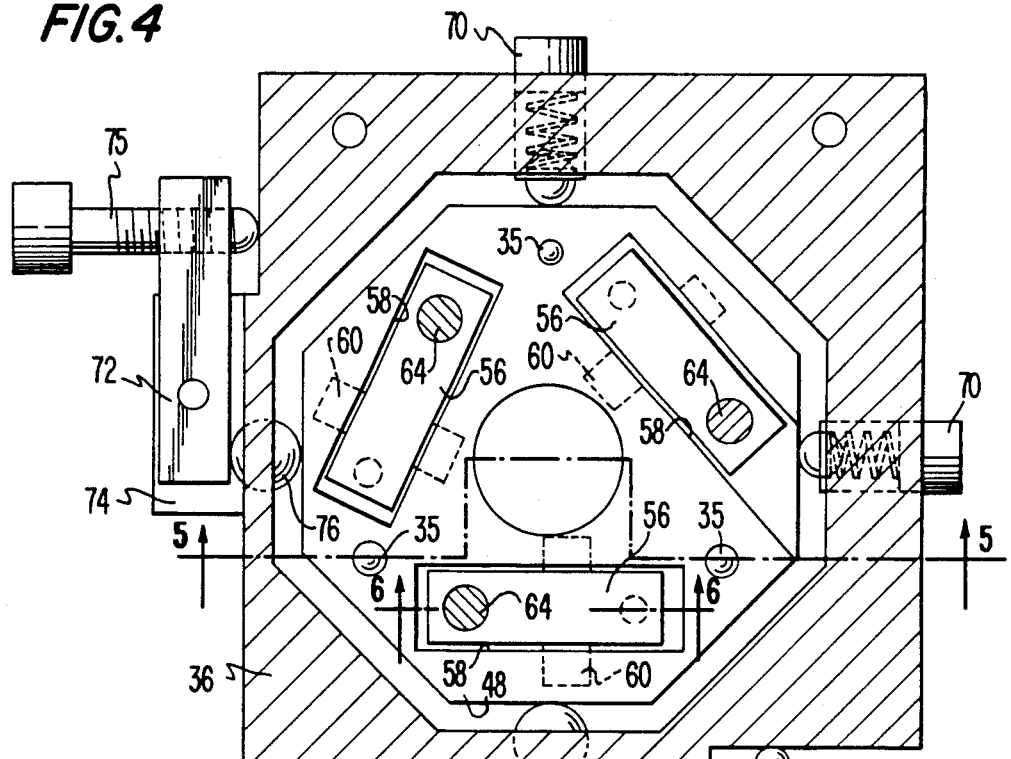
FIG. 4 is a sectional plan view taken along line 4—4 of FIG. 5 showing a fixture for adjusting a mirror in the particle detecting cell of FIG. 1.
Figure 5:
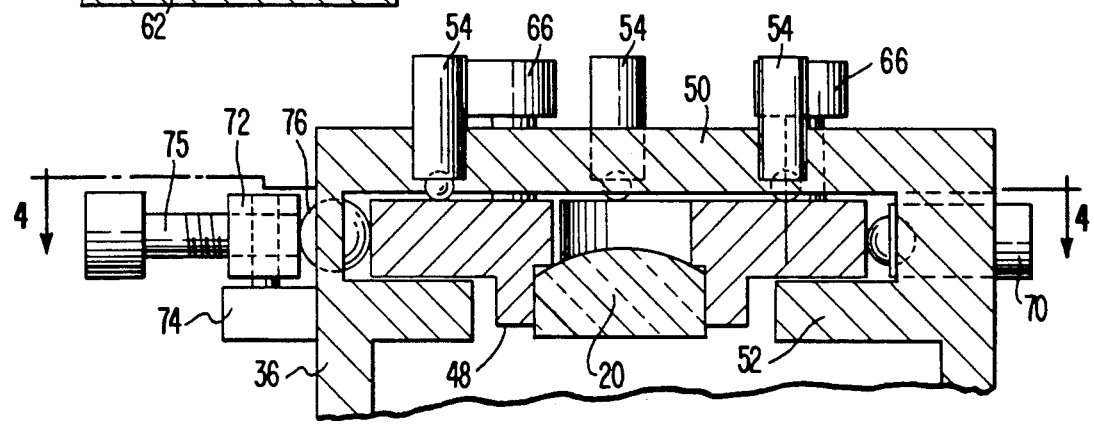
FIG. 5 is a sectional view in elevation of the fixture of FIG. 4 taken along line 5—5 of FIG. 4.

As shown in FIGS. 4 and 5, the mirror block 20 is held in an octagonal support 48, which in turn is supported in an extension of the frame 36 by means of a series of levers and spring-loaded bias members. The frame 36 has a top plate 50 which extends over the top of the octagonal support 48 and a lower circular shelf 52 which surrounds the mirror block 20. The octagonal support is positioned between the top plate 50 and the circular shelf 52. Mounted in the top plate 50 are three spring bias members 54 exerting downward pressure on the support 38 at three equilaterally spaced points 55 as shown in FIG. 4. Within the support 48 are three levers 56 arranged to be parallel to the sides of an equilateral triangle. The levers 56 are mounted to pivot in slots 58 defined in the support 38 on axles 60 mounted in the support 38. Each of the slots 58 is open at the top, but has a bottom wall 62 closing the bottom thereof as shown in the sectional view of FIG. 6. A screw 64 is threaded through one end of each of the levers 56 to engage the bottom wall 62 of the corresponding slot. Each of the screws 64 extends through the top plate 50 and has a head 66 by which the screw can be adjusted. The other end of each of the levers 56 engages a ball 68 captured in an aperture extending through the bottom wall 62 and the ball 68 engages the shelf 52. By adjusting the screw 66, the force exerted by each of the levers 56 upon the ball 68 can be adjusted and thus operate to adjust the angular position of the axis of the mirror block 20 against the downward bias provided by the spring bias members 54. Slight adjustment of the angular position of the axis of the block 20 is permitted by the fact that the bottom surface of the mirror block 20 which is supported on the flat surface 21 of the prism 15 is separated from this surface by a film of liquid. Thus, by means of the screws 64, the axis of the mirror 21 can be adjusted to align precisely with the axis of the laser beam passing through the prism 15.

The liquid of the film separating the mirror block 20 from the prism 15 is a transparent non-volatile relatively viscous fluid which has its index of refraction matched to that of the prism 15 and mirror block. The liquid may be, for example, methylene iodide with synthetics, sulfur and/or iodides added to select the index of refraction. Such liquids with any desired index of refraction over a range to match different indices of refraction of different prism materials are available from R. T. Cargille Laboratories of Cedar Grove, NJ.

As shown in FIG. 4, spring bias members 70 are mounted in the frame 36 to engage the sidewalls of the octagonal support member 48 and bias the octagonal support member 48 to the left and downwardly as shown in FIG. 4. Levers 72 are pivotally mounted on brackets 74 which are fixed to the frame 36 and have screws 75 threaded through one end thereof. The levers 72 engage the octagonal support 48 at the other end thereof by means of ball bearings 76. The ball bearings 76 engage the sidewalls of the octagonal support 38 opposite the bias members 70. By adjusting the screws 75, the levers 72 can be pivoted to adjust the lateral position of the axis of the mirror block 20 so as to align with the axis of the laser beam passing through the prism 15.

The above described specific embodiment is designed to measure the size of particles entrained in water. Similar systems may be used for measuring particles entrained in other transparent liquids. If the liquids have a different index of refraction than water, then the direction of the channel 17 in the prism 15 relative to the diffracted laser beam has to be modified so that the laser beam passes through the glass-liquid interfaces at the brewster angle. In addition, instead of having the particles entrained in liquid, the particles may be entrained in air or gas also requiring a corresponding modification in the brewster angle at the interfaces between the fluid channel and the laser beam.

Figure 7:
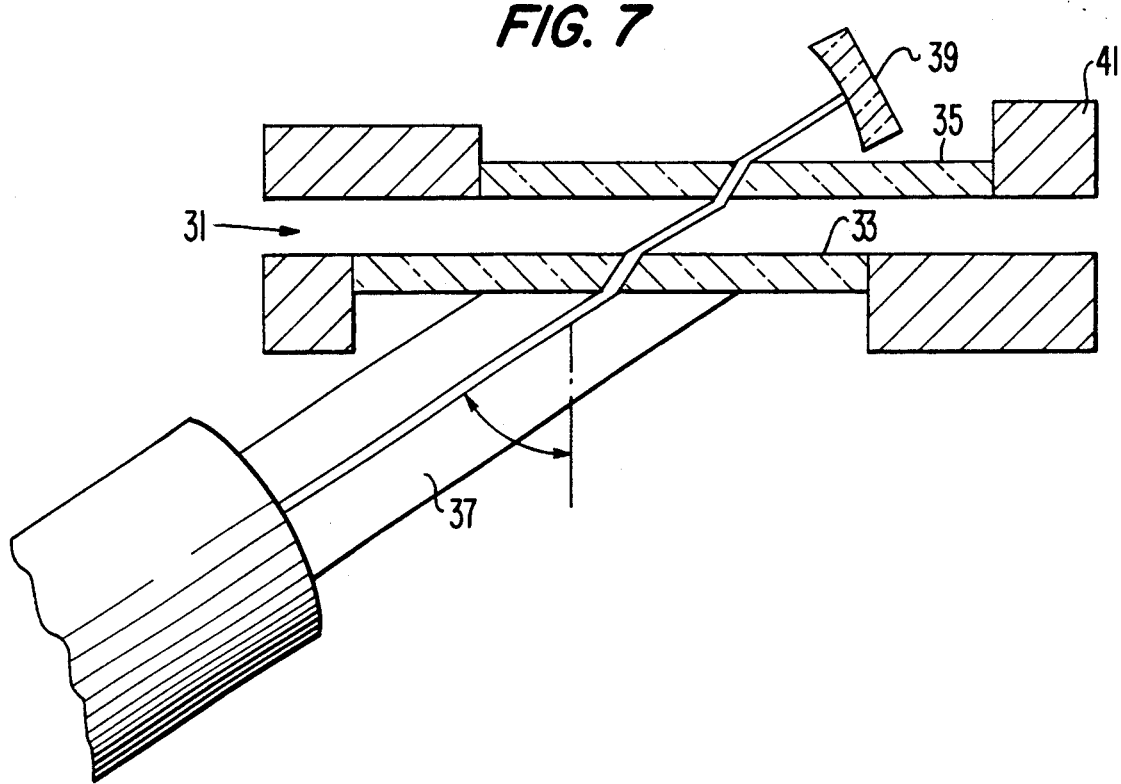
FIG. 7 is a sectional view of a particle detecting cell in accordance With a second embodiment of the invention.
Figure 8:
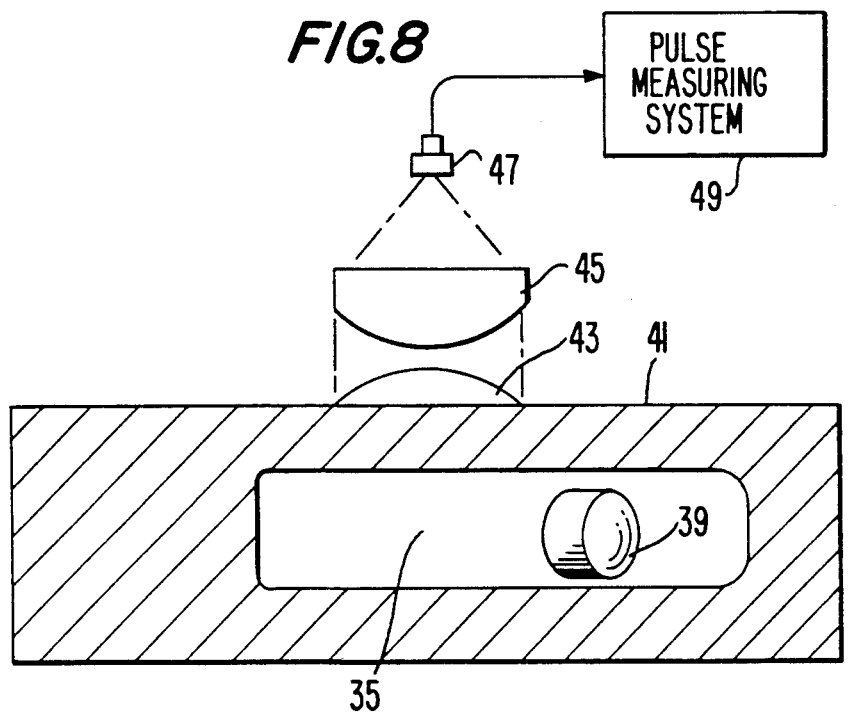
FIG. 8 schematically illustrates a particle measuring instrument showing a top plan view of the particle detecting cell shown in FIG. 7.

FIGS. 7 and 8 illustrate an alternative system designed specifically for measuring the size of particles entrained in a gas stream. As shown in these figures, gas entraining particles to be measured flows in a channel 31 defined between a pair of window panes 33 and 35. A gas laser plasma tube has its beam transmitting end positioned to abut against the window pane 33, which is arranged at the brewster angle with respect to the axis of the plasma tube and the laser beam amplified within the plasma tube. As in the embodiment of FIGS. 1-6, the plasma tube may be provided with its own window, which abuts against the window pane 33, or the window pane 33 may interface directly with the gas of the plasma tube. A spherical mirror 39 is provided on the opposite side of the window pane 35 to reflect the laser beam back to the plasma tube 37 and define an external section for the laser of the plasma tube 37 between the mirror 39 and the window pane 33. The outside and inside walls of each of the windows 33 and 35 define an interface through which the laser beam passes and each of these outside and inside walls must be arranged at the brewster angle with respect to the laser beam. Because the gas entraining the particles flowing in the channel 31 will have essentially the same index of refraction as the gas in the plasma tube 37 as well as the air between the window 37 and mirror 39, essentially an index of refraction of 1, the outside and inside walls of the windows 33 and 35 will all be parallel and the window panes 33 and 35 may be flat panes of glass.

As shown in FIG. 8, the window panes 33 and 35 are mounted in a glass block 41. Light scattered from the laser beam by particles in the channel 31 passes through the glass block 41 and is collected by a lens 43, which is formed in the wall of the glass block 41. The lens 43 collimates the scattered light and directs the scattered light in parallel rays to a lens 45, which focuses scattered light on a photodetector 47. The output pulses of the photodetector 47 produced in response to particles passing through the laser beam are applied to pulse amplitude measuring system 49, which by measuring the amplitude of the pulses from the photodetector 47 measures the size of the particles. The above-description is of preferred embodiments of the invention and modification may be made thereto without departing from the spirit and scope of the invention, which is defined in the appended claims.

I claim:

1. A particle detecting cell comprising a transparent prism defining a fluid channel passing through said prism, means to generate a laser beam to pass through said prism and through said fluid channel, said means to generate a laser beam including a light amplifying section having a transmitting end abutting an external wall of said prism, said external wall being arranged at the brewster angle with respect to the axis of said light amplifying section, said fluid channel being defined by walls arranged at the brewster angle with respect to the laser beam passing through said prism.

2. A particle detecting cell as recited in claim 1, wherein said means to generate a laser beam further comprises a mirror positioned to reflect the laser beam passing through said prism back through said prism into said light amplifying section.

3. A particle detecting cell as recited in claim 2, further comprising means to adjust the angular position of the axis of said mirror for aligning the axis of said mirror with said laser beam passing through said prism.

4. A particle detecting cell as recited in claim 3, further comprising means to adjust the lateral position of said mirror with respect to said laser beam for laterally aligning the axis of said mirror with the axis of said laser beam.

5. A particle size measuring instrument comprising a particle detecting cell as recited in claim 1, and further comprising means to detect light scattered from said laser beam by particles entrained in a fluid passing through said fluid channel.

6. A particle size measuring instrument as recited in claim 5, wherein said means to detect scattered light comprises a photodetector operable to generate a light pulse in response to each particle passing through said laser beam and means to measure the amplitude of each pulse generated by said photodetecting means.

7. A particle detecting cell as recited in claim 1, wherein said light amplifying section comprises a plasma tube.

8. A particle measuring cell comprising a pair of transparent members having parallel inside surfaces defining a fluid passageway, said fluid passageway having an entrance and an exit, means including said inside surfaces and said entrance and said exit to guide continuous flow of a fluid stream through said passageway along an axis extending between said entrance and said exit parallel to said inside surfaces, means including a light amplifying section to generate a laser beam to pass through said fluid passageway, one of said transparent members having an outside surface abutting the transmitting end of said light amplifying section and arranged at the brewster angle with respect to said laser beam passing through said transmitting end of said light amplifying section, said inside surfaces being arranged at the brewster angle with respect to said laser beam passing through said passageway.

9. A particle measuring cell as recited in claim 8, wherein said transparent members comprise glass panes having parallel side walls.

10. A particle measuring instrument comprising a particle cell as recited in claim 9, further comprising means to detect light scattered from said laser beam by particles passing through said laser beam in said fluid channel.

11. A particle measuring instrument as recited in claim 10, wherein said means to detect light scattered from said laser beam comprises photodetecting means to generate electrical pulses in response to each particle passing through said laser beam and means to measure the amplitude of the pulses generated by said photodetecting means.

12. A particle measuring cell as recited in claim 8 wherein said light amplifying section comprises a plasma tube.

* * * * *